United States Patent [19]

Bickman

[11] 4,433,691
[45] Feb. 28, 1984

[54] MOVING TORQUE COIL OSCILLATORY DRIVE MEMBER

[75] Inventor: Bernard F. Bickman, New Brighton, Minn.

[73] Assignee: Honeywell Inc., Minneapolis, Minn.

[21] Appl. No.: 308,706

[22] Filed: Oct. 5, 1981

[51] Int. Cl.³ ................................. A61B 5/10
[52] U.S. Cl. ........................ 128/660; 310/36
[58] Field of Search ............ 128/660, 661, 663; 73/618-620, 633; 310/27, 36-39

[56] References Cited

U.S. PATENT DOCUMENTS

| | | | |
|---|---|---|---|
| 4,092,867 | 6/1978 | Matzuk | 128/660 X |
| 4,120,291 | 10/1978 | Paton et al. | 73/620 |
| 4,151,834 | 5/1979 | Sato et al. | 128/661 X |
| 4,257,272 | 3/1981 | Sloman | 73/633 |
| 4,316,390 | 2/1982 | Kretz | 73/633 X |

Primary Examiner—Kyle L. Howell
Assistant Examiner—Francis J. Jaworski
Attorney, Agent, or Firm—Charles J. Ungemach

[57] ABSTRACT

An oscillatory driving mechanism for use with a scanning transducer includes a configured magnet structure having an associated torque coil cooperating therewith. The torque coil is mounted on a pivoting armature which, in turn, carries the scanning transducer through the predetermined arcuate path. A split pole piece magnetic structure is also positioned adjacent the armature. The armature carries a permanent magnet into an adjustable position relative to the split pole piece members. Hall plate sensors are positioned with respect to the pole piece members to detect the position of the armature at any instant.

8 Claims, 7 Drawing Figures

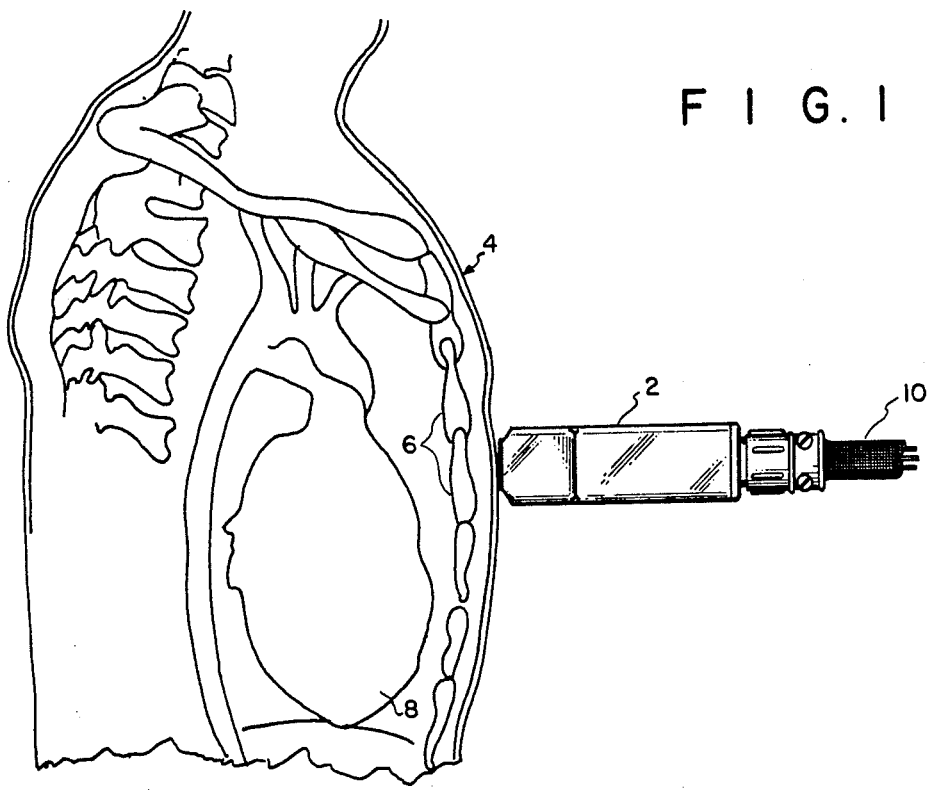
FIG. 1
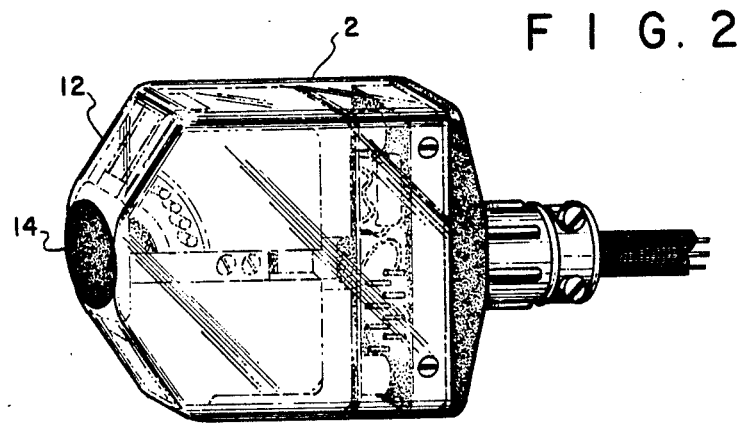
FIG. 2
FIG. 3
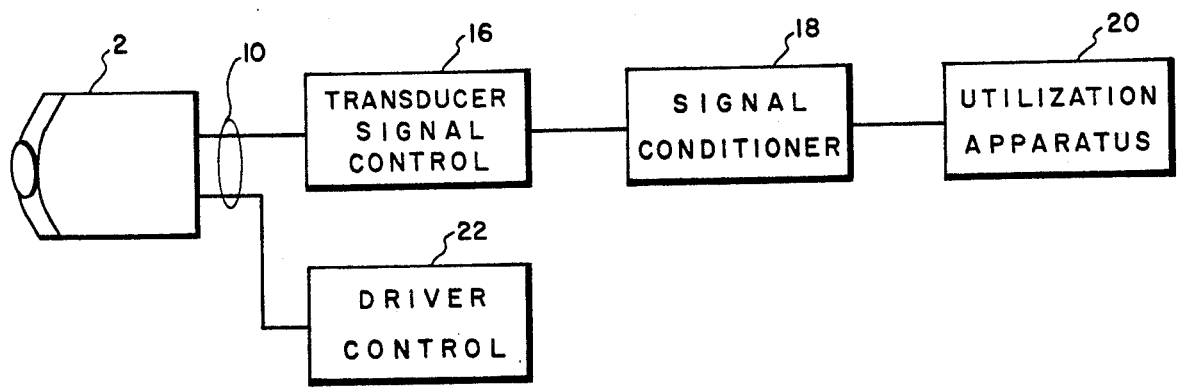

MOVING TORQUE COIL OSCILLATORY DRIVE MEMBER

BACKGROUND OF THE INVENTION

The present invention relates to an oscillatory driving mechanism. More particularly, it relates to a driving mechanism suitable for inclusion in a hand-held ultrasonic scanning transducer.

There have been, provided in the past, hand-held ultrasonic scanning transducer members wherein an oscillatory scanning motion is imparted to an ultrasonic transducer by means of a conventional rotational motor coupled to the scanning transducer by means of complex llinkage means. Although there are advantages to such rotational motor drive mechanisms, such as size, there are disadvantages to such mechanisms found, particularly, in the complexity of the coupling between the conventional rotary motor and the scanning transducer. Such complexities lead to, among other things, higher production costs of the instrument. The complexities of such previous devices have included means for approaching linear velocity of the scanning element during the course of each stroke. Also, in order to synchronize the scanning operation with the subsequent signal processing apparatus, it is necessary to know the instantaneous position of the scanning element during each stroke. Accordingly, there have been provided various techniques for sensing the instantaneous position of the scanning mechanism to provide corresponding signals.

SUMMARY OF THE INVENTION

It is, accordingly, an object of the present invention to provide an improved oscillatory drive mechanism.

It is another object of the present invention to provide a direct drive mechanism or a scanning element without the need for intermediate coupling means.

It is a further object of the present invention to provide an improved drive mechanism as set forth and which includes position detector means.

In accomplishing these and other objects, there has been provided, in accordance with the present invention, an oscillatory driving mechanism for use with a scanning transducer which includes a configured magnet structure having an associated torque coil cooperating therewith. The torque coil is mounted on a pivoting armature which, in turn, carries the scanning transducer through the pedetermined arcuate path. A split pole piece magnetic structure is also positioned adjacent the armature. The armature carries a permanent magnet into an adjustable position relative to the split pole piece members. Hall plate sensors are positioned with respect to the pole piece members to detect the position of the armature at any instant.

BRIEF DESCRIPTION OF THE DRAWINGS

A better understanding of the present invention may be had from the following detailed description when read in the light of the accompanying drawings, in which:

FIG. 1 is a schematic representation of an ultrasonic transducer system which embodies the present invention;

FIG. 2 is a perspective illustration of a transducer head of the type which may incorporate the mechanism of the present invention;

FIG. 3 is a schematic block diagram illustrating a suitable circuit arrangement for use with structures in accordance with the present invention;

DETAILED DESCRIPTION

Figure 7:
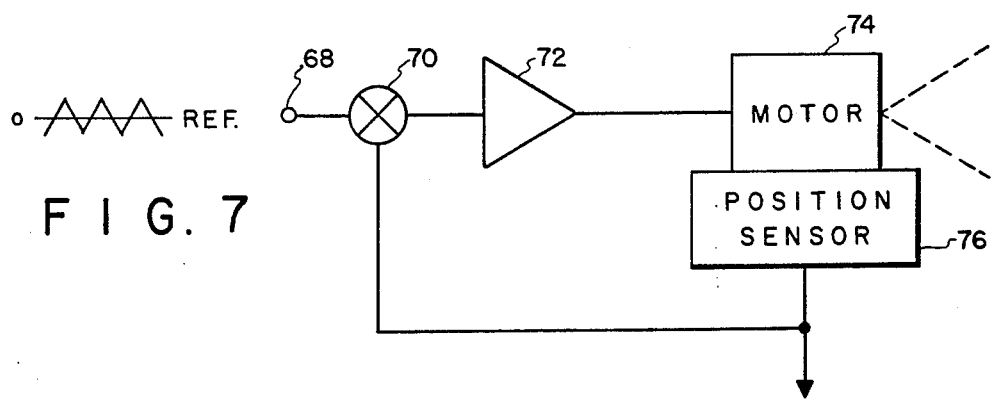
FIG. 7 is a schematic representation of a circuit for the energization of the driver mechanism constructed in accordance with the present invention.

Ultrasonic transducers have been used for non-invasive examination for medical purposes, of the internal organs of a human body. In FIG. 1, there is illustrated such a transducer head 2 positioned adjacent the exterior surface of a human body 4 with the ultrasonic pulses being directed between adjacent ribs 6 thereof toward an internal body organ 8. An electrical cable 10 connects the transducer head 2 to suitable electric circuitry for controlling the operation of the transducer driver and the transducer itself.

In FIG. 2 there is shown a top view of a transducer head 2 including mechanism constructed in accordance with the present invention. In that structure, the transducer assembly mounted in a housing which is basically rectangular in shape but having a symmetrically sloping operating end 12. The sloping operating end 12 terminates in an acoustically permeable diaphragm member 14.

In FIG. 3 the transducer head assembly is connected by the cable 10 first to a transducer signal control circuit 16, from which the pulse signals to energize the transducer are transmitted to the transducer itself. The reflected signals sensed by the transducer are received by the control unit 16 and passed on to subsequent circuitry. That subsequent circuitry includes a signal conditioner circuit 18 wherein the received signals are put in proper form and order for application to a suitable utilization apparatus 20. The utilization apparatus 20 may be in the form of a cathode ray tube display device or, alternatively, a suitable recording instrumentality. Also connected to the head 2 by way of the cable 10 is a driver control circuit 22. More will be said of the driver control circuit 22 hereinafter.

Figure 4:
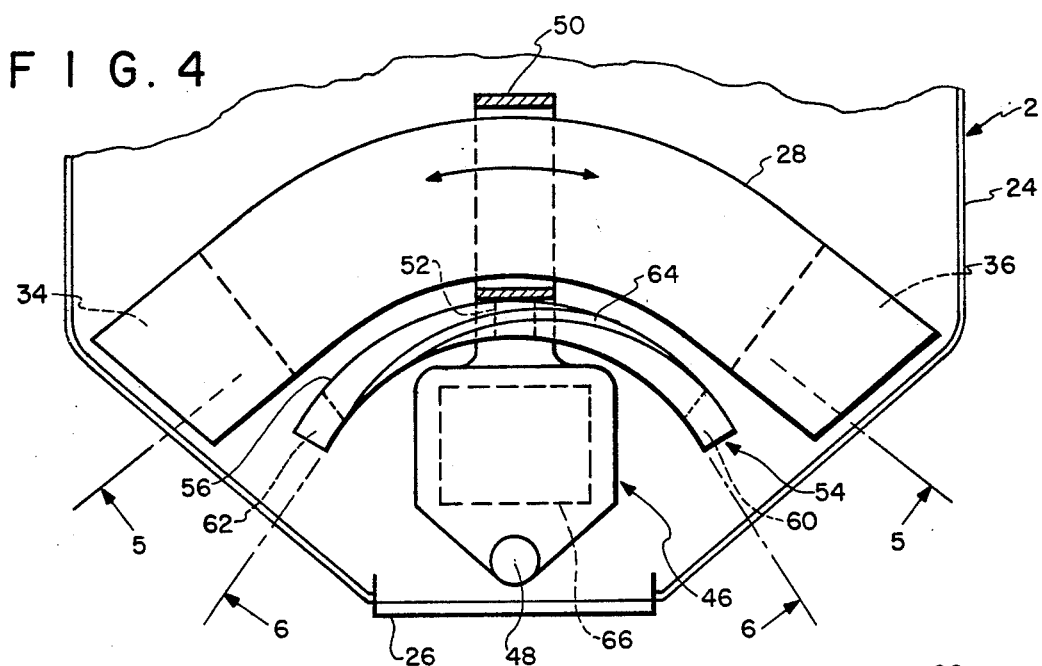
FIG. 4 is a top, broken away view of a driver means constructed in accordance with the present invention.
Figure 5:
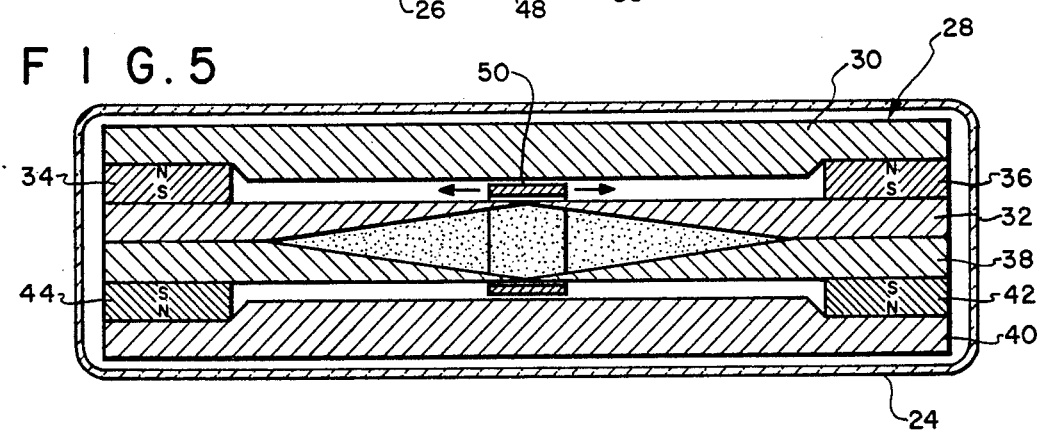
FIG. 5 is a cross-sectional view taken along the line 5—5 of FIG. 4 and viewed in the direction of the appended arrows.
Figure 6:
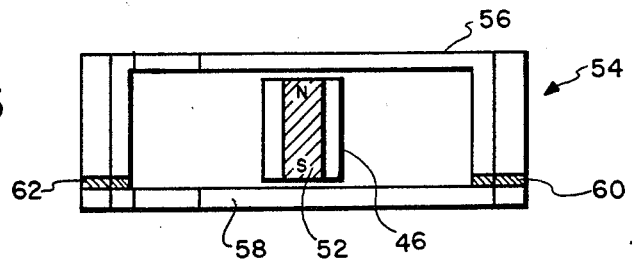
FIG. 6 is a view taken along the line 6—6 of FIG. 4 and viewed in the direction of the appended arrows.

In FIGS. 4, 5, and 6, there is illustrated an embodiment of an oscillatory driver constructed in accordance with the present invention. The transducer head 2 includes a plastic housing 24 which is preferably acoustically opaque. The housing 24 is basically rectangular in configuration but having a truncated tapered front end or operating end. The truncated, symmetrically sloping operating end terminates in an acoustically transparent diaphragm member 26. Supported within the housing 24 there is a driver magnetic pole piece assembly 28. As may be seen from FIG. 4, the pole piece assembly 28 is substantially arcuate in configuration as viewed from the top. From FIG. 5, it may be seen that the transverse configuration of the pole piece assembly is substantially rectangular, formed of a plurality of laminated or sandwiched elements. More specifically, it may be seen that there is provided a first outer pole piece member 30 and a first inner pole piece member 32 sandwiched between the first outer pole piece member 30 and the first inner pole piece member 32 are physically a pair of polarized permanent magnets 34 and 36, respectively. The two magnets 34 and 36 are placed at the outer extremities of the two pole pieces and are dimensioned to define a relatively free space between the outer and inner pole pieces 30 and 32, respectively, and limited at the ends by the two magnets 34 and 36. There is also provided a second inner pole piece member 38 and a second outer pole piece member 40. Here, too, there is a pair of magnets 43 and 44 sandwiched between the outer extremities of the second inner pole piece member 38 and the second outer pole piece member 40. Again the two magnets 42 and 44 are polarized permanent magnets and are dimensioned to define a relatively free space between the outer and inner pole pieces 38 and 40.

An armature assembly 46 is arranged to be oscillated about a pivot point 48. The pivot point 48 is, preferably, located substantially coincident with the center of curvature of the arcuate sections of the pole piece assembly 28. The outer extremity of the armature 46 comprises a torque coil 50 which is configured and dimensioned to ride in the spaces between the two outer pole piece members and the two inner pole piece members effectively surrounding the two inner pole piece members. The torque coil 50 is rigidly secured to and comprises an extension of the armature assembly 46.

As may be seen in FIG. 5, the two inner pole piece members 32 and 38 are each tapered from a minimum thickness dimension at the approximate center line of the pole piece assembly 28 to a maximum or full thickness dimension in the vicinity of the magnetic elements 34, 36, 42, and 44, at the outer extremities of the pole piece assembly 28. Thus, selective energization of the torque coil 50 will cause the armature assembly 46 to be moved to the left or to the right proportionably to the magnitude of the applied signal. More will be said of this relationship hereinafter. The tapering of the two inner pole piece elements define a substantially diamond shaped cavity between them and provides an effective reduction in the electrical time constant of the torque coil 50, thus improving the speed of response. This cavity may be filled with a suitable magnetically inert material such as epoxy.

Also mounted on and carried by the armature assembly 46 is a polarized permanent magnet 52. The permanent magnet 52 comprises a portion of a position sensing arrangement which includes a second or position sensing pole piece assembly 54. This second or sensing pole piece assembly 54 includes an upper pole piece subassembly 56 and a lower pole piece subassembly 58. While either of the two pole piece subassemblies may be a substantially flat planar element with the other being a substantially U-shaped member as shown in FIG. 6, in the examplary embodiment the upper pole piece assembly 56 is shown as the U-shaped structure. Between the ends of the U-shaped structure 56 and the adjacent ends of the other pole piece subassembly 58 there is positioned a first and a second Hall plate sensor 60 and 62, respectively, in the plane as viewed in FIG. 4, both the upper and the lower pole piece subassemblies of the position sensing pole piece assembly 54 are arcuate in configuration having a common center of curvature with the driving pole piece assembly 28. This center of curvature, again, coincides with the pivot point for the armature 46.

As shown most clearly in FIG. 4, either or, preferably, both of the pole piece subassemblies 56 and 58 are formed as two separate arcuate complementary wedge shaped pole pieces. The two separate pole pieces are, of course, of magnetic material but formed into a composite subassembly by a non-magnetic spacing/or bonding agent 64 which may, for example, be brass. With this configuration, as the magnet 52 is moved by the armature to the left or to the right along the arcuate path defined by the pole piece assembly 54, the magnetic field strength sensed by the two Hall plate members 60 and 62, respectively, will vary in accordance with the instantaneous position of the magnet relative to the two complementary wedge shaped pole pieces. With the output signals from the Hall plate members 60 and 62 applied differentially to the input of an associated amplifier, the output signal from that amplifier would be indicative of the instantaneous position of the armature.

Also carried by the armature, in a position between the magnet 52 and the pivot point 48, there is positioned the ultrasonic signal transducer 66. That transducer is positioned to transmit and receive ultrasonic pulse waves through the acoustically transparent diaphragm 26 at the operating end of the transducer assembly 2. As the control signals applied to the torque coil 50 cause the armature 46 to be oscillated back and forth about the pivot axis 48, the direction of the ultrasonic energy transmitted and received by the transducer 66 will be caused to scan a fan shaped sector. This is a desired performance characteristic of such a scanning transducer assembly.

In FIG. 7, there is illustrated a representative driving circuit for energizing the torque coil 50 to cause the desired oscillatory motion of the armature 46. A reference signal is applied to an input terminal 68 and from thence to a summing junction 70. The output from the summing junction is applied as an input signal to an amplifier 72, the output of which is applied to the energizing or torque coil 50 of the driver assembly represented in FIG. 7 as the motor 74. The output signal from the position sensor 76, which includes the position sensor pole piece assembly 54 and the magnet 52 as well as the Hall plate member 60 and 62, is applied as a feedback signal to the summing junction 70. The input reference signal is basically of a sawtooth wave form. The position sensor output signal also applied to the summing junction 70 should be a comparable sawtooth wave form. The two signals combined as input to the amplifier 72 provided, effectively, a closed loop servo-system for driving the motor 74 with the desired oscillatory movement. The output signal from the position sensor 76 is also transmitted to other control circuitry within the signal utilization apparatus 70 whereby to allow an appropriate coordination of the signal with the display apparatus of the utilization system.

As noted, the reference input signal is basically a sawtooth wave shape. The wave shape, however, may be suitably modified to provide the desired linearity of the actual motion of the armature 46 within the drive assembly or motor 74.

Thus there has been provided, in accordance with the present invention, an improved oscillatory drive mechanism suitable for use with a scanning ultrasonic transducer wherein the drive mechanism is directly coupled to the transducer, eliminating the need for intermediate coupling, and which includes an integral position detector means.

The embodiments of the invention in which an exclusive property or privilege is claimed are defined as follows:

1. An oscillatory driver apparatus comprising:

a field pole piece assembly including means defining a fixed polarized magnetic field, said field pole piece assembly being substantially arcuate about a predetermined center of curvature and including a first and a second outer pole piece member and an inner pole piece member, said first and second outer pole piece members being spaced, respectively, from opposite faces of said inner pole piece member, said inner pole piece member being symmetrically tapered from a minimum thickness dimension at the center of said pole piece assembly to a maximum thickness dimension at the ends thereof;

armature means mounted for oscillatory motion about a pivot point coincident with said center of curvature, said armature means including a torque coil mounted to be operative in said polarized magnetic field with said torque coil being mounted to surround said inner pole piece member and to operate in the spaces between said inner pole piece member and said outer pole piece members;

means for selectively energizing said torque coil with an oscillatory signal to produce a controlled magnetic field which reacts with said fixed polarized magnetic field to impart a magnetomotive force to said armature in accordance with the selective energization therof; and signal transducing means mounted on and carried by said armature whereby a scanning oscillatory motion is imparted to said transducer directly by said armature.

2. A driver apparatus as set forth in claim 1 wherein said inner pole piece includes a first and a second inner pole piece element, both of said elements being tapered from said minimum to said maximum and defining a substantially diamond shaped cavity between them, said cavity being filled with a non-magnetic filler.

3. A driver apparatus as set forth in claim 1 wherein means defining said fixed polarized magnetic field includes permanent magnet means positioned between each end of each of said outer pole piece members and said inner pole piece member, said permanent magnet means being polarized to make said inner pole piece member of one magnetic polarity and each of said outer pole piece members of the opposite magnetic polarity.

4. A driver apparatus as set forth in claim 1 including position sensing means coupled to said armature to produce a signal indicative of the instantaneous position of said armature and wherein said position sensing means comprises a permanent magnet mounted on and carried by said armature and adetector means positioned to respond to the field of said permanent magnet to produce said signal indicative of the position of said armature.

5. A driver apparatus as set forth in claim 4 wherein said detector means comprises a magnetic pole piece assembly, said detector magnetic pole piece assembly being substantially arcuate about said center of curvature and including a first and a second pole piece element, said first and second pole piece elements being substantially complementary wedges separated by a non-magnetic bonding medium, said detector means further including Hall plate sensors mounted in the magnetic flux path of said detector pole piece means at the opposite ends of said detector pole piece assembly, said Hall plate sensors responding differentially to said field of said permanent magnet and therefore to the position of said armature.

6. A driver apparatus as set forth in claim 1 wherein said signal transducing means comprises an ultrasonic transducer for ultrasonic imaging of anatomical members.

7. An oscillatory driver apparatus for a signal transducer, said apparatus comprising:
a field poled piece assembly including means establishing a first magnetic field of fixed polarization;
said field pole piece assembly being substantially arcuate about a predetermined center of curvature;
said field pole piece assembly including a portion which is tapered from a minimum thickness dimension at the center of said pole piece assembly to a maximum thickness dimension at the ends thereof;
an armature means mounted for oscillatory motion about a pivot point coincident with said center of curvature;
said armature means including a torque coil mounted to the operative in said first magnetic field;
means for selectively energizing said torque coil with an oscillatory signal to produce a controlled magnetic field which reacts with said first magnetic field to impart a magnetomotive force to said armature in accordance with the selective energization thereof; and
said signal transducer being mounted on and carried by said armature whereby a scanning oscillatory motion is imparted to said signal transducer directly by said armature.

8. A driver apparatus as set forth in claim 7 and further including position sensor means coupled to said armature to produce a position signal indicative of the instantaneous position of said armature; and
means coupling at least a portion of said position signal in feedback relation to said means for energizing said torque coil to provide a closed-loop control therefor.

* * * * *